United States Patent [19]

Mizutani et al.

[11] Patent Number: 4,875,924
[45] Date of Patent: Oct. 24, 1989

[54] CINNOLINE DERIVATIVE, PROCESS FOR PREPARING THE SAME AND HERBICIDAL COMPOSITION CONTAINING THE SAME

[75] Inventors: Masato Mizutani, Toyonaka; Masao Shiroshita, Nishinomiya; Masaharu Sakaki; Hiroki Okuda, both of Toyonaka; Nobuaki Mito, Takarazuka, all of Japan

[73] Assignee: Sumitomo Chemical Company, Limited, Osaka, Japan

[21] Appl. No.: 137,626

[22] Filed: Dec. 24, 1987

[30] Foreign Application Priority Data

Dec. 25, 1986 [JP] Japan ................... 61-309981

[51] Int. Cl.$^4$ ............... C07D 237/28; A01N 43/58
[52] U.S. Cl. ....................... 71/92; 544/235; 564/34
[58] Field of Search ............... 544/235; 71/92

[56] References Cited

U.S. PATENT DOCUMENTS 4,729,782  3/1988  Labovitz et al. ............... 544/235

FOREIGN PATENT DOCUMENTS 0138661  4/1985  European Pat. Off. ............ 544/235

OTHER PUBLICATIONS

Prudchenko et al., Chemical Abstracts, vol. 69, No. 36059g (1968).
Sandison et al., J. Chem. Soc. Chem. Comm., 1974, p. 752.
Ames et al., Synthesis, 1983, p. 52.

Primary Examiner—Mukund J. Shah
Assistant Examiner—E. Bernhardt
Attorney, Agent, or Firm—Armstrong, Nikaido, Marmelstein, Kubovcik & Murray

[57] ABSTRACT

A cinnoline derivative having the formula (I):

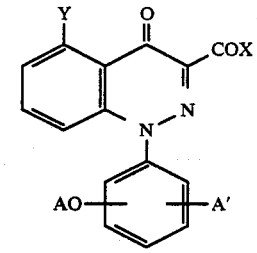

in which X is —OH, —O$^-$M$^+$, —OR$^1$ or

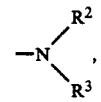

wherein
M$^+$ is an alkali metal cation, an alkaline earth

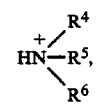

in which R$^4$, R$^5$ and R$^6$ are the same or different and each is hydrogen atom, a C$_1$–C$_6$ alkyl group, a C$_3$–C$_4$ alkenyl group, a C$_3$–C$_4$ alkynyl group, a C$_3$–C$_8$ cycloalkyl group, benzyl group or phenyl group; R$^1$ is a C$_1$–C$_9$ alkyl group, a C$_3$–C$_6$ alkenyl group, a C$_3$–C$_4$ alkynyl group, a C$_1$–C$_3$ alkoxy (C$_1$–C$_4$) alkyl group, a C$_1$–C$_3$ haloalkyl group, a C$_3$–C$_8$ cycloalkyl group, benzyl group or phenyl group; and R$^2$ and R$^3$ are the same or different and each is hydrogen atom, a C$_1$–C$_6$ alkyl group, a C$_3$–C$_4$ alkenyl group, a C$_3$–C$_4$ alkynyl group, a C$_3$–C$_8$ cycloalkyl group, a benzyl group in which at most two of hydrogen atoms at the α-position thereof may be substituted by methyl group, a C$_2$–C$_3$ hydroxyalkyl group or a phenyl group in which at most three of hydrogen atoms thereof may be substituted by the same or different C$_1$–C$_2$ alkyl group or halogen atom;
Y is fluorine atom, chlorine atom, bromine atom, a trihalomethyl group, a C$_1$–C$_6$ alkoxy group or a C$_1$–C$_2$ alkyl group;
A is a C$_1$–C$_3$ polyhaloalkyl group; and
A' is hydrogen atom, fluorine atom, chlorine atom or bromine atom,
a process for preparing the same, and a herbicidal composition containing the same as an active ingredient,
a method for controlling undesired weeds using the same, and use of the same as a herbicide.

7 Claims, No Drawings

CINNOLINE DERIVATIVE, PROCESS FOR PREPARING THE SAME AND HERBICIDAL COMPOSITION CONTAINING THE SAME

BACKGROUND OF THE INVENTION

The present invention relates to novel cinnoline derivatives, processes for preparing the cinnoline derivatives and herbicidal compositions containing the cinnoline derivatives as an active ingredient. The present invention further relates to a method for controlling undesired weeds used the cinnoline derivatives and use of the cinnoline derivatives as a herbicide.

Some 1-aryl-1,4-dihydro-4-oxocinnoline-3-carboxylic acid derivatives have been hitherto reported in literatures such as Zh. Obshch. Khim., vol. 37, p. 2487 (1967), J. Chem. Soc. Chem., Comm., p. 752 (1974), Synthesis, p. 52 (1983), and Japanese Unexamined Patent Publication (Tokkyo Kokai) No. 249972/1986. However, there has not been reported that cinnoline derivatives in the present invention have herbicidal activity.

SUMMARY OF THE INVENTION

As a result of the eager study for providing a novel herbicide, it has now been found that cinnoline derivatives having the formula (I):

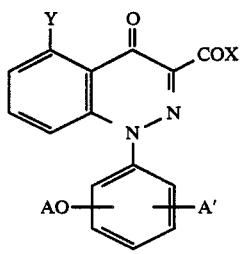

in which X is —OH, —O⁻M⁺, —OR¹ or

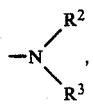

wherein
M⁺ is an alkali metal cation, an alkaline earth metal cation or

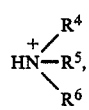

in which $R^4$, $R^5$ and $R^6$ are the same or different and each is hydrogen, a $C_1$-$C_6$ alkyl, a $C_3$-$C_4$ alkenyl, a $C_3$-$C_4$ alkynyl, a $C_3$-$C_8$ cycloalkyl, benzyl or phenyl; $R^1$ is a $C_1$-$C_9$ alkyl, a $C_3$-$C_6$ alkenyl, a $C_3$-$C_4$ alkynyl, a $C_1$-$C_3$ alkoxy ($C_1$-$C_4$) alkyl, a $C_1$-$C_3$ haloalkyl, a $C_3$-$C_8$ cycloalkyl, benzyl or phenyl; and $R^2$ and $R^3$ are the same or different and each is hydrogen, a $C_1$-$C_6$ alkyl, a $C_3$-$C_4$ alkenyl, a $C_3$-$C_4$ alkynyl, a $C_3$-$C_8$ cycloalkyl, a benzyl in which at most two of hydrogen atoms at the α-position thereof may be substituted by methyl, a $C_2$-$C_3$ hydroxyalkyl or a phenyl in which at most three hydrogen atoms thereof may be substituted by the same or different $C_1$-$C_2$ alkyl or halogen;

Y is fluorine, chlorine, bromine, a trifluoromethyl, a $C_1$-$C_6$ alkoxy or a $C_1$-$C_2$ alkyl;

A is $CF_3$, $CHF_2$, $CF_2Br$, $CF_2CHF_2$, $CH_2CF_3$, $CF_2CHCl_2$, $CFClCHFCl$, $CF_2CHFCl$, or $CF_2CHFCF_3$; and A' is hydrogen, fluorine, chlorine or bromine exhibit both excellent herbicidal activity and selectivity between crops and weeds, and thus the present invention has been accomplished.

In accordance with the present invention, there are provided a cinnoline derivative having the formula (I):

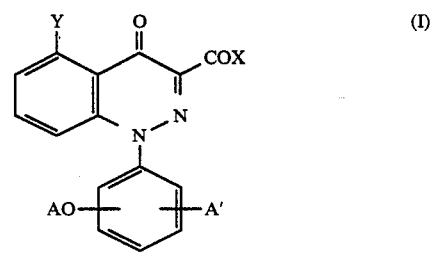

in which X, Y, A and A' are as defined above, a process for preparing it, a herbicidal composition containing it as an active ingredient, a method for controlling undesired weeds using it and use of it as a herbicide.

DETAILED DESCRIPTION

Among the cinnoline derivatives having the formula (I) of the present invention, cinnoline derivatives having —OH, —O⁻M⁺ or —OR¹ as X are preferable because of the highly herbicidal activity against weeds. Further, among them, cinnoline derivatives having difluoromethyl group or trifluoromethyl group as A are more preferable. Moreover, among them, cinnoline derivatives having fluorine atom, chlorine atom or bromine atom, trifluoromethyl group or a $C_1$-$C_4$ alkoxy group are still more preferable.

Hereinafter, processes for preparing the cinnoline derivatives of the present invention are explained.

In the compounds of the present invention, a cinnoline derivatives having the formula (I-a):

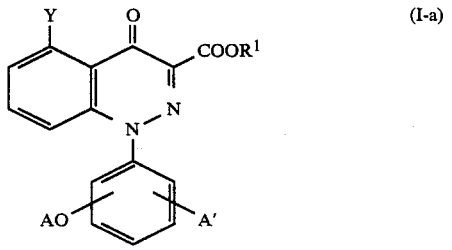

in which $R^1$, Y, A and A' are as defined above can be prepared by reacting a hydrazone having the formula (II):

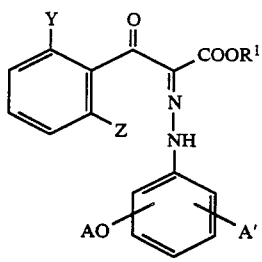

(II)

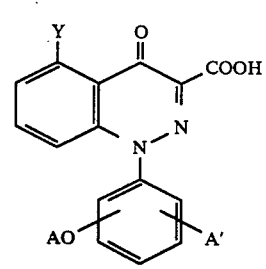

(I-b)

in which R[1], Y, A and A' are as defined above and Z is a fluorine atom, chlorine atom or bromine atom provided that when Y is fluorine atom, Z is fluorine atom and that when Y is bromine atom, Z is fluorine atom or bromine atom and a dehydrohalogenating agent.

The above reaction is usually carried out without any solvent or in a solvent, at a temperature of 0° to 150° C., for a period of 10 minutes to 20 hours. The dehydrohalogenating agent may be used in an amount of 1 to 10 equivalents to one equivalent of the hydrazone (II).

Examples of the solvent are, for instance, aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. acetone, methyl ethyl ketone, methyl isobutyl ketone, isophorone, cyclohexanone), esters (e.g. ethyl formate, ethyl acetate, butyl acetate, diethyl carbonate), nitro compounds (e.g. nitroethane, nitrobenzene), nitriles (e.g. acetonitrile, isobutylnitrile), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethyl sulfoxide, sulfolane), water, and the like. Their mixtures are also usable.

Examples of the dehydrohalogenating agent are, for instance, organic bases (e.g. pyridine, triethyl amine, N,N-diethylaniline), inorganic bases (e.g. sodium hydroxide, patassium hydroxide, sodium carbonate, patassium carbonate, sodium hydride), alkali metal alkoxide (e.g. sodium methoxide, sodium ethoxide), and the like.

For the purpose of conducting the reaction more efficiently, quaternary ammonium salts and crown ethers can be added. Examples of the quaternary ammonium salts are, for instance, benzyl triethyl ammonium chloride, tetrabutyl ammonium chloride, and the like. Examples of the crown ethers are, for instance, dibenzo-18-crown-6, and the like.

After completion of the reaction, the reaction mixture is subjected to ordinary post-treatment such as addition of water followed by collection of precipitated crystals, extraction by an organic solvent, or concentration. If necessary, a purification procedure such as chromatography or recrystallization may be adopted. Thus the cinnoline derivative (I-a) of the present invention can be obtained.

In the compounds of the present invention, a cinnoline derivative having the formula (I-b):

in which Y, A, and A' are as defined above can be prepared by hydrolyzing the cinnoline derivative (I-a).

The above reaction is carried out in water or a mixed solvent of water and an alcohol (e.g. methanol, ethanol, isopropanol, diethylene glycol, glycerin), an ether (e.g. tetrahydrofuran, dioxane), a nitrile (e.g. acetonitrile), an acid amide (e.g. formamide, N,N-dimethylformamide) or a sulfur compound (e.g. dimethyl sulfoxide). Usually the acid or the alkali is added in an amount of 1 to 100 equivalents to one equivalent the cinnoline derivative (I-a). The reaction temperature is 20° to 100° C. The reaction period is 30 minutes to 10 hours.

Examples of the acid are, for instance, hydrochloric acid, sulfuric acid, nitric acid, and the like. Examples of the alkali are, for instance, sodium hydroxide, potassium hydroxide, and the like. When the alkali is used, the reaction mixture is neutralized with hydrochloric acid, sulfuric acid, nitric acid, formic acid, acetic acid, or the like after completion of the reaction.

After completion of the reaction, the reaction mixture is subjected to ordinary post-treatment such as collection of precipitated crystals, extraction by an organic solvent, or concentration. If necesarry, a purification procedure such as chromatography or recrystallization may be adopted. Thus the cinnoline derivative (I-b) of the present invention can be obtained.

In the compounds of the present invention, a cinnoline derivative having the formula (I-c):

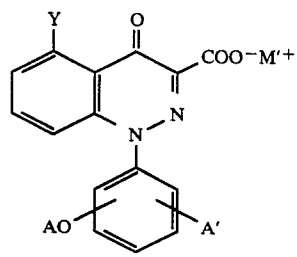

(I-c)

wherein Y, A and A' are as defined above, and M'+ is an alkali metal cation or an alkaline earth metal cation can be prepared by reacting the cinnoline derivative (I-b) and a hydroxide having the formula (III):

(III)

wherein M'+ is as defined above.

The above reaction is usually carried out in water at a temperature of 0° to 50° C. for a period of 5 minutes to 5 hours. The hydroxide (III) may be used in an amount of 0.7 to 1 equivalent to one equivalent of the cinnoline derivative (I-b).

Examples of the hydroxide (III) are, for instance, lithium hydroxide, sodium hydroxide, potassium hydroxide, calcium hydroxide, and the like.

After completion of the reaction, if necessary, the water layer is washed with an organic solvent, and then concentrated. Thus the cinnoline derivative (I-c) of the present invention can be obtained.

In the compounds of the present invention, a cinnoline derivative having the formula (I-d):

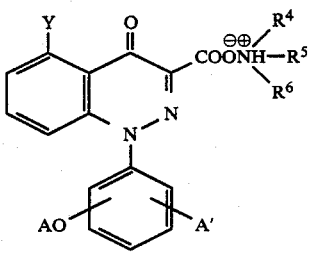 (I-d)

wherein $R^4$, $R^5$, $R^6$, Y, A and A' are as defined above can be prepared by reacting the cinnoline derivative (I-b) and an amine having the formula (IV):

 (IV)

wherein $R^4$, $R^5$ and $R^6$ are as defined above.

The above reaction is usually carried out without any solvent or in a solvent, at a temperature of 0° to 100° C., for a period of 5 minutes to 3 hours. The amine (IV) may be used in an amount of 1 to 10 equivalents to one equivalent of the cinnioline derivative (I-b).

Examples of the solvent are, for example, aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), alcohols (e.g. methanol, ethanol, isopropanol, t-butanol, octanol, cyclohexanol, methyl cellosolve, diethylene glycol, glycerin), esters (e.g. ethyl formate, ethyl acetate, butyl acetate, diethyl carbonate), nitro compounds (e.g. nitroethane, nitrobenzene), nitriles (e.g. acetonitrile, isobutylnitrile), water, and the like. Their mixtures are also usuable.

After completion of the reaction, the reaction mixture is subjected to ordinary post-treatment such as concentration. If necessary, a purification procedure such as recrystallization may be adopted. Thus the cinnoline derivative (I-d) can be obtained.

In the compounds of the present invention, a cinnoline derivative (I-e):

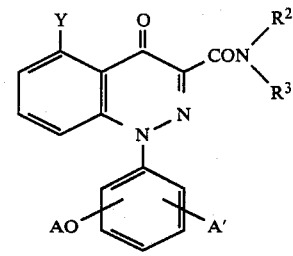 (I-e)

wherein $R^2$, $R^3$, Y, A and A' are as defined above can be prepared by reacting a halide having the formula (V):

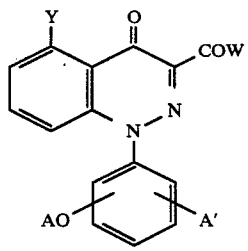 (V)

wherein Y, A and A' are as defined above and W is a halogen atom and an amine having the formula (VI):

 (VI)

wherein $R^2$ and $R^3$ are as defined above.

The above reaction is usually carried out without any solvent or in a solvent, in the presence of a dehydrohalogenating agent, at a temperature of 0° to 50° C., for a period of 10 minutes to 3 hours. The amine (VI) and the dehydrohalogenating agent are used in an amount of 1 to 5 equivalents and 1 to 2 equivalents respectively, to one equivalent of the halide (V).

Examples of the solvents are, for instance, apliphatic hydrocarbons (e.g. hexane, heptane, ligroin, petrodeum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), esters (e.g. ethyl formate, ethyl acetate, butyl acetate, diethyl carbonate), nitro compounds (e.g. nitroethane, nitrobenzene), nitriles (e.g. acetonitrile, isobutylnitrile), tertiary amines (e.g. pyridine, triethylamine, N,N-diethylaniline, tributylamine, N-methylmorpholine), acid amides (e.g. formamide, N,N-dimethylformamide, acetamide), sulfur compound (e.g. dimethyl sulfoxide, sulfolane), water, and the like. Their mixtures are also usable.

Examples of the dehydrohalogenating agent are, for instnace, organic bases (e.g. pyridine, triethyl amine, N,N-diethyl aniline), and the like.

After completion of the reaction, the reaction mixture is subjected to ordinary post-treatment such as extraction with an organic solvent or concentration. If necessary, a purification procedure such as chromatography or recrystallization may be adopted. Thus the cinnoline derivative (I-e) can be obtained.

The halide (V) is easily prepared by usual acid halogenation of the cinnoline derivative (I-b).

Typical examples of the cinnoline derivatives which can be prepared according to the above procedure are shown in Table 1.

TABLE 1

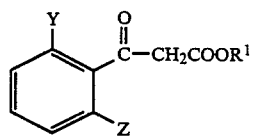

| OA | A' | X | Y |
|---|---|---|---|
| 4-OCF₃ | H | OH | F |
| " | " | OK | " |
| " | " | ONH₄ | " |
| " | " | OC₂H₅ | " |
| " | " | N(C₂H₅)₂ | " |
| " | " | N(CH₂CH=CH₂)₂ | " |
| " | " | OH | Cl |
| " | " | OK | " |
| " | " | OC₂H₅ | " |
| " | " | 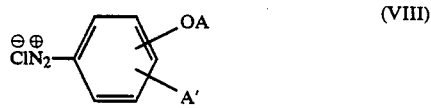 | " |
| " | " | OC₂H₅ | CF₃ |
| " | " | OK | Br |
| " | " | OCH₃ | CH₃ |
| " | " | ONa | OCH₃ |
| 4-OCF₃ | H | OK | OC₄H₉(n) |
| 3-OCF₃ | " | OC₂H₅ | Cl |
| 4-OCHF₂ | " | OH | F |
| " | " | OK | " |
| " | " | OCH₃ | " |
| " | " | OC₂H₅ | " |
| " | " | OH | Cl |
| " | " | ONa | " |
| " | " | OC₂H₅ | " |
| " | " | OC₄H₉(n) | " |
| " | " | OC₄H₉(i) | " |
| " | " | OC₃H₇(n) | CF₃ |
| " | " | OK | OC₂H₅ |
| " | " | ONa | CH₃ |
| " | " | OH | OCH₃ |
| " | 2-F | OK | F |
| " | " | OC₂H₅ | Cl |
| 2-OCHF₂ | 4-F | OK | CF₃ |
| " | " | OCH₃ | OC₃H₇(i) |
| 3-OCHF₂ | H | OC₂H₅ | Cl |
| 4-OCF₂Br | " | OK | F |
| " | " | OC₂H₅ | Cl |
| " | " | ONa | CF₃ |
| 4-OCF₂CHF₂ | " | " | F |
| " | " | OH | Cl |
| " | " | OK | " |
| " | " | OC₂H₅ | " |
| " | " | OCH₃ | Br |
| 4-OCH₂CF₃ | " | OC₂H₅ | F |
| " | " | OH | Cl |
| " | " | ONa | " |
| " | " | OC₂H₅ | " |
| 4-OCH₂CF₃ | H | OC₄H₉(n) | Cl |
| 4-OCF₂CHCl₂ | " | OH | F |
| 4-OCFClCHFCl | " | OC₂H₅ | Cl |
| 4-OCF₂CHFCl | " | OK | OCH₃ |
| 4-OCF₂CHFCF₃ | " | OC₂H₅ | F |

In preparing the compounds of the present invention, the hydrazone derivative (II), which is the strating material, can be prepared by reacting a ketoester having the formula (VII):

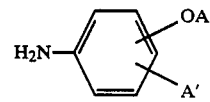

in which R¹, Y and Z are as defined above and a diazonium salt having the formula (VIII):

$$\ominus\oplus \atop ClN_2-\underset{A'}{\underset{|}{\diagdown}}-OA \qquad (VIII)$$

in which A and A' are as defined above.

The above reaction is usually carried out in a solvent at a temperature of 0° to 50° C. for a period of 10 minutes to 5 hours. The diazonium salt (VIII) may be used in an amount of 0.7 to 1.5 equivalents to one equivalent of ketoester (VII).

Examples of the solvent are, for instance, ethers (e.g. diethyl ether, diisopropyl ether, dioxane, tetrahydrofuran, diethylene glycol dimethyl ether), alcohols (e.g. methanol, ethanol, isopropanol, t-butanol, octanol, cyclohexanol, methyl cellosolve, diethylene glycol, glycerin), tertiary amines (e.g. pyridine, triethylamine, N,N-diethylaniline, tributylamine, N-methylmorpholine), acid amides (e.g. formamide, N,N-dimethylformamide, acetamide), water, and the like. Their mixture are also usable.

For the purpose of conducting the reaction more efficiently, inorganic bases (e.g. sodium carbonate, potassium carbonate, sodium acetate, potassium acetate) can be added to the reaction system.

After completion of the reaction, the reaction mixture is subjected to ordinary post-treatment such as extraction with an organic solvent or concentration. If necessary, a purification procedure such as chromatography or recrystallization may be adopted. Thus the desired starting material (II) can be obtained.

The diazonium salt (VIII) is prepared according to an ordinary process from an aniline having the formula (IX):

$$H_2N-\underset{A'}{\underset{|}{\diagdown}}-OA$$

in which A and A' are as defined above.

The compounds of the present invention show an excellent herbicidal activity and an excellent selectivity between crops and weeds. That is, in upland fields, by soil treatment of foliage treatment, the cinnoline derivatives of the present invention exhibit a herbicidal activity against undesired weeds, for instance, broad-leaved weeds such as wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), shepherdspurse (*Capsella bursapastoris*), velvetleaf (*Abutilon theophrasti*), prickly sida (*Sida spinosa*), field pansy (*Viola arvensis*), cleavers (*Galium aparine*), field bindweed (*Convolvulus arvensis*), purple deadnettle (*Lamium purpureum*), henbit (*Lamium amplexicaure*), jimsonweed (*Datura stramonium*), black nightshade (*Solanum nigrum*), persian speedwell (*Veronica persica*), scentless chamomile (*Matricaria perforata*) and corn marigold (*Chrysanthemum segetum*); graminaceous weeds such as Japanese millet (*Echinochloa frumentacea*), barnyardgrass (*Echinochloa crus-galli*), green foxtail (*Setaria virides*), large crabgrass (*Digitaria sanguinalis*), annual bluegrass (*Poa annua*), blackgrass (*Alopecurus myosuroides*), oats (*Avena sativa*), wild oat (*Avena fatua*), johnsongrass (*Sorghum halepense*), quackgrass (*Agropyron repens*), downy brome (*Bromus tectorum*), bermudagrass (*Cynodon dactylon*); commelinaceous weeds such as asiatic dayflower (*Commelina communis*); cyperaceous weeds such as purple nutsedge (*Cyperus rotundus*); and the like. The cinnoline derivatives of the present invention do not exert any material phytotoxicity to main crops such as corn, wheat, rice, soybean, cotton and sugar beat.

The cinnoline derivatives of the present invention also exhibit a herbicidal activity on various lowland weeds in question, for instance, graminaceous weeds such as barnyardgrass (*Echinochloa oryzicola*); broad-leaved weeds such as common falsepimpernel (*Lindernia procumbens*), indian toothcup (*Rotala indica*) and waterwort (*Elatine triandra*); cyperaceous weeds such as smallflower umbrellaplant (*Cyperus difformis*), hardstem bulrush (*Scirpus juncoides*), needle spikerush (*Eleocharis acicularis*) and water nutsedge (*Cyperus serotinus*); and the like without exerting any material phtotoxicity to rice plants in treatment under flooded condition.

When the cinnoline derivatives are employed as an active ingredient in a herbicidal composition of the present invention, they are usually formulated in the form of emulsifiable concentrates, wettable powders, suspensions, granules and the like in combination with auxiliary agents such as a solid carrier, liquid carrier and surface active agent. The content of the cinnoline derivatives of the present invention as the active ingredient in such formulations is within a range of 0.1 to 90% by weight, preparably 0.2 to 80% by weight.

Examples of the solid carrier are, for instance, fine powders or granules of kaolin clay, attapulgite clay, bentonite, terra alba, pyrophyllite, talc, diatomaceous earth, calcite, walnut powders, urea, ammonium sulfate, synthetic hydrous silicate, and the like. Examples of the liquid carrier are, for instance, aromatic hydrocarbons (e.g. xylene, methylnaphthalene), alcohols (e.g. isopropanol, ethylene glycol, cellosolve), ketones (e.g. acetone, cyclonhexanone, isophorone), vegetable oils (e.g. soybean oil, cotton seed oil), dimethylsulfoxide, N,N-dimethylformamide, acetonitrile, water, and the like.

Examples of the surface active agent used for emulsification, dispersion or wetting are, for instance, anionic surface active agents such as alkylsulfates, alkylsulfonates, alkylarylsulfonates, dialkylsulfosuccinates and phosphates of polyoxyethylenealkylaryl ethers; nonionic surface active agents such as polyoxyethylene alkyl ethers, polyoxyethylene alkylaryl ethers, polyoxyethylene polyoxypropylene block copolymer, sorbitan fatty acid esters and polyoxyethylene sorbitan fatty acid esters; and the like.

Examples of the auxiliary agents other than above are, for instance, ligninsulfonates, alginates, polyvinyl alcohols, gum arabic, CMC (carboxymethylcellulose), PAP (isopropyl acid phosphate), and the like.

As the method for controlling undesired weeds of the present invention, the cinnoline derivatives of the present invention are usually formulated and used in soil treatment, foliage treatment or treatment under flooded condition before the emergence of weeds or within about one month after the emergence of weeds to the area where undesired weeds grow or will grow. Soil treatment includes soil surface treatment, soil incorporation treatment, and the like. The foliage treatment includes, in addition to the treatment of the plant over the top, directed application wherein herbicides are applied only to weeds so as not to attach to crops, and the like.

The cinnoline derivatives of the present invention may be used together with other herbicides to improve their activity as herbicides. Further, they may applied in combination with insecticides, acaricides, nematocides, fungicides, plant growth regulators, fertilizers, soil improvers, and the like.

Furthermore, the cinnoline derivatives of the present invention can be used as an active ingredient of a herbicide for paddy field, upland field, orchard, pasture land, lawn, forest, non-agricultural field, and the like.

The dosage rate of the cinnoline derivatives of the present invention varies depending on weather conditions, preparation form, prevailing season, mode of application, soil involved, crop and weed species aimed at, and the like. Generally, however, the dosage rate is from 0.5 to 500 grams, preferably from 1 to 300 grams of the active ingredient per are. The herbicidal composition of the invention formulated into emulsifiable concentrate, a wettable powder, a suspension, or the like is ordinarily employed by diluting a designed amount of it with ater, if necessary with addition of an auxiliary agent such as a spreading agent, at a volume of 1 to 10 liters per are. The herbicidal composition formulated into granule and the like is usually applied without any dilution.

Examples of the wetting agent are, in addition to the surface active agents as noted above, for instance, polyoxyethylene resin acid (ester), ligninsulfonate, abiethylenic acid salt, dinaphthylmethanedisulfonate, paraffin, and the like.

The present invention is more specifically described and explained by means of the following Examples, Reference Example, Formulation Examples and Test Examples, wherein the compound Nos. of the active ingredient corresponds to those in Table 2. It is to be understood that the present invention is not limited to the Examples, Formulation Examples, and Test Examples and various changes and modifications may be made in the invention without departing from the spirit and scope thereof.

EXAMPLE 1

[Preparation of the compound No. 3]

Ethyl 2-[(4-trifluoromethoxyphenyl)-1,1-diazanediyl]-2,6-difluorobenzoylacetate (4.24 g), potassium carbonate (1.41 g) and dibenzo-18-crown-6 (10 mg) were added to N,N-dimethylformamide (20 ml), and the resultant mixture was heated at 100° C. for 1 hour. The mixture was cooled to room temperature, and was poured into ice-water (100 ml). After allowing it to stand for 2 hours, the precipitated crystals were collected by filtration. The crystals were washed with water (20 ml) two times and were dried under reduced pressure to give 3.93 g of desired ethyl 1-(4-trifluoromethoxyphenyl)-1,4-dihydro-4-oxo-5-fluorocinnolin-3-carboxylate (yield: 97.3%). m.p., 178.0° C.

EXAMPLE 2

[Preparation of the compound No. 26]

Ethyl 2-[(4-difluoromethoxyphenyl)-1,1-diazanediyl]-2,6-dichlorobenzoylacetate (4.30 g) and potassium carbonate (1.50 g) were added to N,N-dimethylformamide (25 ml), and the resultant mixture was heated at 100° C. for 1.5 hours. The mixture was cooled to room temperature, and was poured into ice-water (100 ml) to precipitate crystals. The precipitated crystals were collected by filtration, washed with water (20 ml), and recrystallized from ethanol to give 3.68 g of desired ethyl 1-(4-difluoromethoxyphenyl)-1,4-dihydro-4-oxo-5-chlorocinnoline-3-carboxylate (yield: 93.4%). m.p., 134° C.

EXAMPLE 3

[Preparation of the compound No. 1]

Ethyl 1-(4-trifluoromethoxyphenyl)-1,4-dihydro-4-oxo-5-fluorocinnoline-3-carboxylate (2.31 g) and potassium hydoxide (0.67 g) were added to a mixed solvent of ethanol (24 ml) and water (6 ml), and the resultant mixture was stirred at 60° to 70° C. for 7 hours. After being allowed to cool to room temperature, the mixture was diluted with water (100 ml), and washed with diethyl ether (30 ml). The water layer was neutralized with concentrated hydrochloric acid to pH 2 to precipitate crystals. The precipitated crystals was collected by filtration, washed two times with water (20 ml), and dried under reduced pressure to give 2.14 g of desired 1-(4-trifluoromethoxyphenyl)-1,4-dihydro-4-oxo-5-fluorocinnoline-3-carboxylic acid (yield: 99.5%). m.p., 200° C. (decomposed)

EXAMPLE 4

[Preparation of the compound No. 2]

1-(4-Trifluoromethoxyphenyl)-1,4-dihydro-4-oxo-5-fluorocinnoline-3-carboxylic acid (405 mg) and a 0.827M aqueous solution of potassium hydroxide (1.21 ml) were added to water (10 ml), and the mixture was stirred at room temperature for 3 hours. The resultant mixture was washed with ethyl acetate (10 ml). After removing the water, the obtained crystals was dried to give 406 mg of desired potassium 1-(4-trifluoromethoxyphenyl)-1,4-dihydro-4-oxo-5-fluorocinnoline-3-carboxylic (yield: 100%). m.p., 198°–213° C. (decomposed)

EXAMPLE 5

[Preparation of the compound No. 4]

1-(4-Trifluoromethoxyphenyl)-1,4-dihydro-4-oxo-5-fluorocinnoline-3-carboxylic acid (368 mg), thionyl chloride (179 mg) and pyridine (50 mg) were dissolved in toluene (10 ml), and the obtained solution was heated under reflux for 2 hours. After being allowed to cool to room temperature, the resultant mixture was added dropwise to a solution which was obtained by dissolving diethylamine (146 mg) and triethylamine (152 mg) in ethyl acetate (10 ml). The obtained mixture was stirred at room temperature for 3 hours, and was allowed to stand overnight. After the reaction solution was poured into diluted hydrochloric acid (30 ml) to which ice was added, the resultant mixture was extracted two times with ethyl acetate (20 ml). The organic layer was washed with a saturated aqueous sodium bicarbonate (10 ml), a saturated saline water (10 ml), and then dried over anhydrous magnesium sulfate, and was concentrated. The residue was purified by silica gel column chromatography (eluent: n-hexane-acetone) to give 143 mg of desired N,N-diethyl-1-(4-trifluoromethoxyphenyl)-1,4-dihydro-4-oxo-5-fluorocinnoline-3-carboxyamide (yield: 33.8%). m.p., 118.5° C.

Some of the cinnoline derivatives of the present invention obtained according to these process as above are shown in Table 2.

TABLE 2

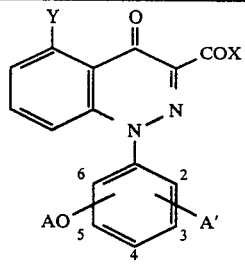

[I]

| Compound No. | OA | A' | X | Y | physical properties |
|---|---|---|---|---|---|
| 1 | 4-OCF$_3$ | H | OH | F | mp 200–205° C. (dec) |
| 2 | " | " | OK | " | mp 198–213° C. (dec) |
| 3 | " | " | OC$_2$H$_5$ | " | mp 178.0° C. |
| 4 | " | " | N(C$_2$H$_5$)$_2$ | " | mp 118.5° C. |
| 5 | " | " | 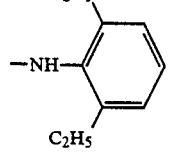 | " | mp 194.0° C. |

TABLE 2-continued

[Structure I: A quinoline/cinnoline-type compound with substituents Y, O, COX, and a phenyl group with AO at position 5/6 and A' at position 2/3, numbered 2,3,4,5,6]

| Compound No. | OA | A' | X | Y | physical properties |
|---|---|---|---|---|---|
| 6 | " | " | OH | Cl | mp 210° C. |
| 7 | " | " | OK | " | mp 262° C. |
| 8 | " | " | OC$_2$H$_5$ | " | mp 114.6° C. |
| 9 | " | " | " | Br | mp 110–120° C. |
| 10 | " | " | " | CH$_3$ | mp 90.6° C. |
| 11 | " | " | OH | CF$_3$ | mp 238–240° C. |
| 12 | " | " | ONa | " | mp 182–187° C. |
| 13 | " | " | OC$_2$H$_5$ | " | mp 133° C. |
| 14 | " | " | OH | OCH$_3$ | mp 265–269° C. |
| 15 | " | " | ONa | " | mp 215–220° C. |
| 16 | " | " | OC$_2$H$_5$ | " | mp 154.2° C. |
| 17 | " | " | " | OC$_2$H$_5$ | mp 142.4° C. |
| 18 | 3-OCF$_3$ | " | OH | F | mp 233.8° C. |
| 19 | " | " | ONa | " | mp 170–175° C. |
| 20 | " | " | OC$_2$H$_5$ | " | mp 130.0° C. |
| 21 | 4-OCHF$_2$ | " | OH | " | mp 270–276° C. |
| 22 | " | " | OK | " | mp 198–210° C. (dec) |
| 23 | " | " | OC$_2$H$_5$ | " | mp 137.6° C. |
| 24 | " | " | OH | Cl | mp 228° C. |
| 25 | " | " | ONa | " | mp 199° C. |
| 26 | " | " | OC$_2$H$_5$ | " | mp 134° C. |
| 27 | " | " | OC$_4$H$_9$(n) | " | n$_D^{22.5}$ 1.5890 |
| 28 | " | " | OC$_4$H$_9$(i) | " | mp 111° C. |
| 29 | " | " | OC$_2$H$_5$ | Br | mp 142.8° C. |
| 30 | " | " | " | CH$_3$ | mp 158.5° C. |
| 31 | 4-OCHF$_2$ | H | OH | CF$_3$ | mp 244.7° C. |
| 32 | " | " | ONa | " | mp 182–195° C. |
| 33 | " | " | OC$_2$H$_5$ | " | mp 133–136° C. |
| 34 | " | " | " | OCH$_3$ | mp 135.4° C. |
| 35 | " | " | " | OC$_2$H$_5$ | mp 174.6° C. |
| 36 | 2-OCHF$_2$ | 4-F | OH | F | mp 229.9° C. |
| 37 | " | " | ONa | " | mp 195–198° C. |
| 38 | " | " | OC$_2$H$_5$ | " | mp 161.6° C. |
| 39 | " | " | OH | Cl | mp 221.2° C. |
| 40 | " | " | ONa | " | mp 210–215° C. |
| 41 | " | " | OC$_2$H$_5$ | " | mp 226.4° C. |
| 42 | 4-OCF$_2$CHF$_2$ | H | " | F | mp 180.9° C. |
| 43 | " | " | " | Cl | mp 133° C. |
| 44 | 4-OCH$_2$CF$_3$ | " | " | F | mp 115.6° C. |
| 45 | " | " | OH | Cl | mp 276° C. |
| 46 | " | " | ONa | " | mp 201° C. |
| 47 | " | " | OC$_2$H$_5$ | " | mp 142° C. |
| 48 | " | " | OC$_4$H$_9$(n) | " | n$_D^{22.5}$ 1.5785 |

An example of process for preparing the hydrazone derivative [II], which is the starting material, is shown in the following Reference Example.

REFERENCE EXAMPLE 1

To 4-trifluoromethoxyaniline (551 mg) was added water (6 ml) and concentrated hydrochloric acid (2 ml) to prepare a solution of hydrochloric acid salt. To the solution was added dropwise a solution of sodium nitrite (236 mg) in water (2 ml) over about 5 minutes to form a diazonium salt. The obtained solution was added dropwise to a solution of ethyl 2,6-difluorobenzoyl acetate (710 mg) in a mixed solvent of 70% methanol (15 ml) and pridine (2 ml) at 10° to 20° C. over above 10 minutes. After completion of the addition, the reaction mixture was stirred at room temperature for 1 hour. After adding water (30 ml), the resultant mixture was extracted with ethyl acetate (30 ml) two times. After the mixture was extracted, the residue was purified by means of silica gel column chromatography (eluent: n-hexane-ethyl acetate) to give 1048 mg of ethyl 2-[(4-trifluoromethoxyphenyl)-1,1-diazanediyl]-2,6-difluorobenzoylacetate (yield: 80.9%). m.p., 77.3° C.

Formulation Examples are shown below. In the Formulation Examples, all parts are by weight.

FORMULATION EXAMPLE 1

Fifty parts of the compound No. 13, 3 parts of calcium ligninsulfonate, 2 parts of sodium laurylsulfate and 45 parts of synthetic hydrous silicate were well mixed to obtain a wettable powder.

FORMULATION EXAMPLE 2

The parts of the compound No. 3, 8, 9, 10, 13 or 16, 14 parts of polyoxyethylenestyrylphenyl ether, 6 parts of calcium dodecylbenzenesulfonate, 30 parts of xylene and 40 parts of cyclohexanone were well mixed to obtain an emulsifiable concentrate.

FORMULATION EXAMPLE 3

Two parts of the compound No. 33, 1 part of synthetic hydrous silicate, 2 parts of calcium ligninsulfonate, 30 parts of bentonite and 65 parts of kaolin clay were well pulverized and mixed together. The mixture was then kneaded with water, granulated and dried to obtain a granule.

FORMULATION EXAMPLE 4

Twenty-five parts of the compound No. 17, 3 parts of polyoxyethylene sorbitan monooleate, 3 parts of CMC and 69 parts of water were mixed and pulverized until the particle size of the mixture became not more than 5 microns to obtain a suspension.

The herbicidal activity of the compounds are illustratively shown in the following Test Examples wherein the degree of germination and the degree of growth inhibition are observed with the naked eye and herbicidal activity is rated with an index 0, 1, 2, 3, 4, 5, 6, 7, 8, 9 or 10, in which the numeral "0" indicates no material difference is seen in comparison with the untreated plant and the numeral "10" indicates the complete inhibition or death of the test plants. Compound A and Compound B used for comparison are shown in Table 3.

TABLE 3

| Compound No. | formula | remarks |
|---|---|---|
| A | | coumarin |
| B | | The compound disclosed in Japanese Unexamined Patent Publication No. 249972/1986 |

TEST EXAMPLE 1

The seeds of Japanese millet, oats, radish and velvetleaf were sowed in cylindrical plastic pots (diameter, 10 cm; height, 10 cm) filled with plow-field soil, and cultivated at room temperature for 10 days. A designed amount of the test compound formulated into emulsifiable concentrate according to Formulation Example 2 was diluted with water containing a spreading agent, and the dilution was sprayed over the foliage of the test plants by means of a small sprayer at a spray volume of 10 liters per are. The test plants were further grown in a greenhouse for 20 days, and the herbicidal activity was rated. The results are shown in Table 4.

TABLE 4

| Compound No. | Dosage (g/are) | Herbicidal activity | | | |
|---|---|---|---|---|---|
| | | Japanese millet | Oats | Radish | Velvetleaf |
| 1 | 40 | 9 | 9 | 9 | — |
| | 10 | 7 | 7 | — | — |
| 2 | 40 | 9 | 9 | 9 | 7 |
| | 10 | 7 | 7 | 8 | — |
| 3 | 40 | 7 | 9 | 8 | 4 |
| | 10 | 3 | 3 | 4 | 4 |
| 6 | 40 | 8 | 9 | 7 | — |
| | 10 | — | 6 | — | — |
| 7 | 40 | 9 | 9 | 7 | — |
| | 10 | 8 | 8 | 5 | — |
| 8 | 40 | 10 | 9 | 9 | — |
| | 10 | 9 | 8 | 8 | — |
| 13 | 40 | 10 | 10 | 9 | — |
| | 10 | 9 | 9 | 7 | — |
| 17 | 40 | 10 | 10 | 10 | 9 |
| | 10 | 9 | 8 | 7 | 6 |
| 22 | 40 | 9 | 9 | 9 | 6 |
| | 10 | 7 | 7 | 6 | — |
| 23 | 40 | 8 | 8 | 8 | 7 |
| | 10 | 6 | 6 | 5 | 5 |
| 24 | 40 | 10 | 8 | 9 | — |
| | 10 | 9 | 7 | 7 | — |
| 25 | 40 | 10 | 10 | 10 | — |
| | 10 | 8 | 7 | 8 | — |
| 27 | 40 | 10 | 10 | 10 | — |
| | 10 | 8 | 7 | 7 | — |
| 28 | 40 | 10 | 10 | 10 | — |
| | 10 | 7 | 8 | 7 | — |
| 34 | 40 | 8 | 10 | 9 | 8 |
| | 10 | 6 | 8 | 6 | 6 |
| A | 40 | 1 | 0 | 2 | 0 |
| | 10 | 0 | 0 | 0 | 0 |
| B | 40 | 5 | 0 | 4 | 2 |
| | 10 | 0 | 0 | 0 | 0 |

TEST EXAMPLE 2

Cylindrical plastic pots (diameter, 8 cm; height, 12 cm) were filled with paddy field soil, and the seeds of barnyardgrass were sowed in 1 to 2 cm depth. Water was poured therein to make a flooded condition. Rice seedlings of 2-leaf stage were transplanted therein, and the test plants were grwon in a greenhouse. Six days (at that time weeds began to germinate) thereafter, a designed amount of the test compound formulated into emulsifiable concentrate according to Formulation Example 2 and diluted with water (5 ml) was applied to the water surface. The test plants were grown for further 20 days in the greenhouse, and the herbicidal activity was rated. The results are shown in Table 5.

TABLE 5

| Compound No. | Dosage (g/are) | Herbicidal activity | |
|---|---|---|---|
| | | Rice | Barnyardgrass |
| 1 | 10 | — | 10 |
| | 2.5 | 0 | 9 |
| 3 | 40 | 1 | 9 |
| | 10 | 0 | 5 |
| 8 | 40 | 1 | 10 |
| | 10 | 0 | 10 |
| 10 | 40 | 1 | 10 |
| | 10 | 0 | 8 |
| 13 | 10 | 1 | 10 |
| | 2.5 | 0 | 8 |
| 23 | 40 | 2 | 10 |
| | 10 | 0 | 8 |
| 26 | 40 | 0 | 10 |
| | 10 | 0 | 8 |
| 28 | 40 | 0 | 10 |
| | 10 | 0 | 10 |
| 29 | 40 | 0 | 10 |
| | 10 | 0 | 9 |
| 33 | 40 | 1 | 10 |

TABLE 5-continued

| Compound No. | Dosage (g/are) | Herbicidal activity | |
|---|---|---|---|
| | | Rice | Barnyardgrass |
| | 10 | 0 | 10 |
| 38 | 40 | 0 | 10 |
| | 10 | 0 | 10 |
| 41 | 40 | 0 | 10 |
| | 10 | 0 | 8 |
| A | 40 | 0 | 0 |
| | 10 | 0 | 0 |
| B | 40 | 6 | 9 |
| | 10 | 4 | 5 |

TEST EXAMPLE 3

Paddy field soil was filled in 1/5000 are Wagner's pots, and the seeds of barnyardgrass were incorporated from 1 to 2 cm deep in the soil. After creating the state of paddy field by flooding, rice plants in a 3-leaf stage were transplanted and cultivated in a greenhouse. After 4 days, the prescribed amount of the emulsifiable concentrates of the test compounds prepared according to Formulation Example 2 was diluted with 10 ml of water and applied to the water surface, and the depth of water was made 4 cm. After treatment, the test plants were cultivated for 20 days in a greenhouse to examine the herbicidal activity and phytotoxicity. The results are shown in Table 6. In this test water leakage corresponding to a water level of 3 cm/day was carried out for 2 days from the day subsequent to the treatment.

TABLE 6

| Compound No. | Dosage (g/are) | Herbicidal activity | |
|---|---|---|---|
| | | Rice | Barnyardgrass |
| 8 | 40 | 2 | 10 |
| | 10 | 0 | 9 |
| 13 | 10 | 3 | 10 |
| | 2.5 | 0 | 10 |
| 33 | 40 | 2 | 10 |
| | 10 | 0 | 10 |
| A | 40 | 0 | 0 |
| | 10 | 0 | 0 |
| B | 40 | 5 | 8 |
| | 10 | 3 | 4 |

In addition to ingredients used in the Examples, Reference Example, Formulation Examples and Test Examples, other ingredients can be used in the Examples as set forth in the specification to obtain substantially the same results.

What we claim is:

1. A cinnoline derivative having the formula (I):

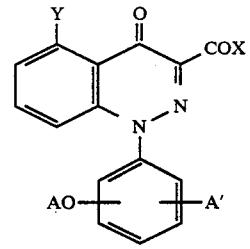

in which
X is —OH, —O⁻M⁺, —OR¹ or

wherein
M⁺ is an alkali metal cation, an alkaline earth metal cation or

in which $R^4$, $R^5$ and $R^6$ are the same or different and each is hydrogen atom, $C_1$-$C_6$ alkyl, $C_3$-$C_4$ alkenyl, $C_3$-$C_4$ alkynyl, $C_3$-$C_8$ cycloalkyl, benzyl or phenyl; $R^1$ is $C_1$-$C_9$ alkyl, $C_3$-$C_6$ alkenyl, $C_3$-$C_4$ alkynyl, $C_1$-$C_3$ alkoxy ($C_1$-$C_4$) alkyl, $C_3$-$C_8$ cycloalkyl, benzyl or phenyl; and $R^2$ and $R^3$ are the same or different and each is hydrogen, $C_1$-$C_6$ alkyl, $C_3$-$C_4$ alkenyl, $C_3$-$C_4$ alkynyl, $C_3$-$C_8$ cycloalkyl, benzyl in which at most two hydrogen atoms at the α-position thereof may be substituted by methyl, $C_2$-$C_3$ hydroxyalkyl or phenyl in which at most three of hydrogen atoms thereof may be substituted by the same or different $C_1$-$C_2$ alkyl;
Y is fluorine, chlorine, bromine, trifluoromethyl, $C_1$-$C_6$ alkoxy or $C_1$-$C_2$ alkyl;
A is $CF_3$, $CHF_2$, $CF_2Cl$, $CF_2Br$, $CF_2CHF_2$, $CH_2CF_3$, $CF_2CHCl_2$, $CFClCHFCl$, $CF_2CHFCl$ or $CF_2CHFCF_3$; and
A' is hydrogen, fluorine, chlorine or bromine.

2. The cinnoline derivative of claim 1, in which X is —OH, —O⁻M⁺ or —OR¹.

3. The cinnoline derivative of claim 2, in which A is difluoromethyl or trifluoromethyl.

4. The cinnoline derivative of claim 3, in which Y is fluorine, chlorine, or bromine.

5. The cinnoline derivative of claim 3, in which Y is trifluoromethyl.

6. The cinnoline derivative of claim 3, in which Y is $C_1$-$C_4$ alkoxy.

7. A method for controlling undesired weeds, which comprises applying a herbicidally effective amount of the compound according to claim 1 and an agriculturally acceptable carrier or diluent to the area where undesired weeds grow or will grow.

* * * * *